(12) United States Patent
Caldwell

(10) Patent No.: US 8,607,805 B2
(45) Date of Patent: Dec. 17, 2013

(54) ORAL HYGIENE SYSTEM

(76) Inventor: Larry Caldwell, Sugar Land, TX (US)

( * ) Notice: Subject to any disclaimer, the term of this patent is extended or adjusted under 35 U.S.C. 154(b) by 0 days.

(21) Appl. No.: 13/045,097

(22) Filed: Mar. 10, 2011

(65) Prior Publication Data
US 2012/0055504 A1    Mar. 8, 2012

Related U.S. Application Data

(60) Provisional application No. 61/313,248, filed on Mar. 12, 2010.

(51) Int. Cl.
*A61C 15/00* (2006.01)
*A45D 44/18* (2006.01)
*A46B 7/04* (2006.01)

(52) U.S. Cl.
USPC .......... 132/323; 132/309; 15/176.4; 15/176.5

(58) Field of Classification Search
USPC ............... 132/308–311, 321–329; 15/167.1, 15/176.1; 433/141, 142, 147
See application file for complete search history.

(56) References Cited

U.S. PATENT DOCUMENTS

| | | | | | |
|---|---|---|---|---|---|
| 4,751,761 | A | * | 6/1988 | Breitschmid | 15/176.5 |
| 5,027,467 | A | * | 7/1991 | Tarrson et al. | 15/167.1 |
| 5,127,415 | A | * | 7/1992 | Preciutti | 132/323 |
| 5,293,661 | A | * | 3/1994 | Appleby | 15/167.1 |
| 5,758,382 | A | * | 6/1998 | Maekawa et al. | 15/167.1 |
| 6,170,111 | B1 | * | 1/2001 | Rueb et al. | 15/106 |

* cited by examiner

*Primary Examiner* — Robyn Doan
(74) *Attorney, Agent, or Firm* — Conley Rose, P.C.

(57) ABSTRACT

An oral hygiene system including a handle with a releasable locking mechanism. The system also includes an oral hygiene attachment removably coupled to the handle. The locking mechanism includes a safety gate coupled to the handle, the safety gate being pivotable relative to the handle. The locking mechanism also includes a locking receptacle configured to receive the safety gate, whereby the locking mechanism is locked.

17 Claims, 5 Drawing Sheets

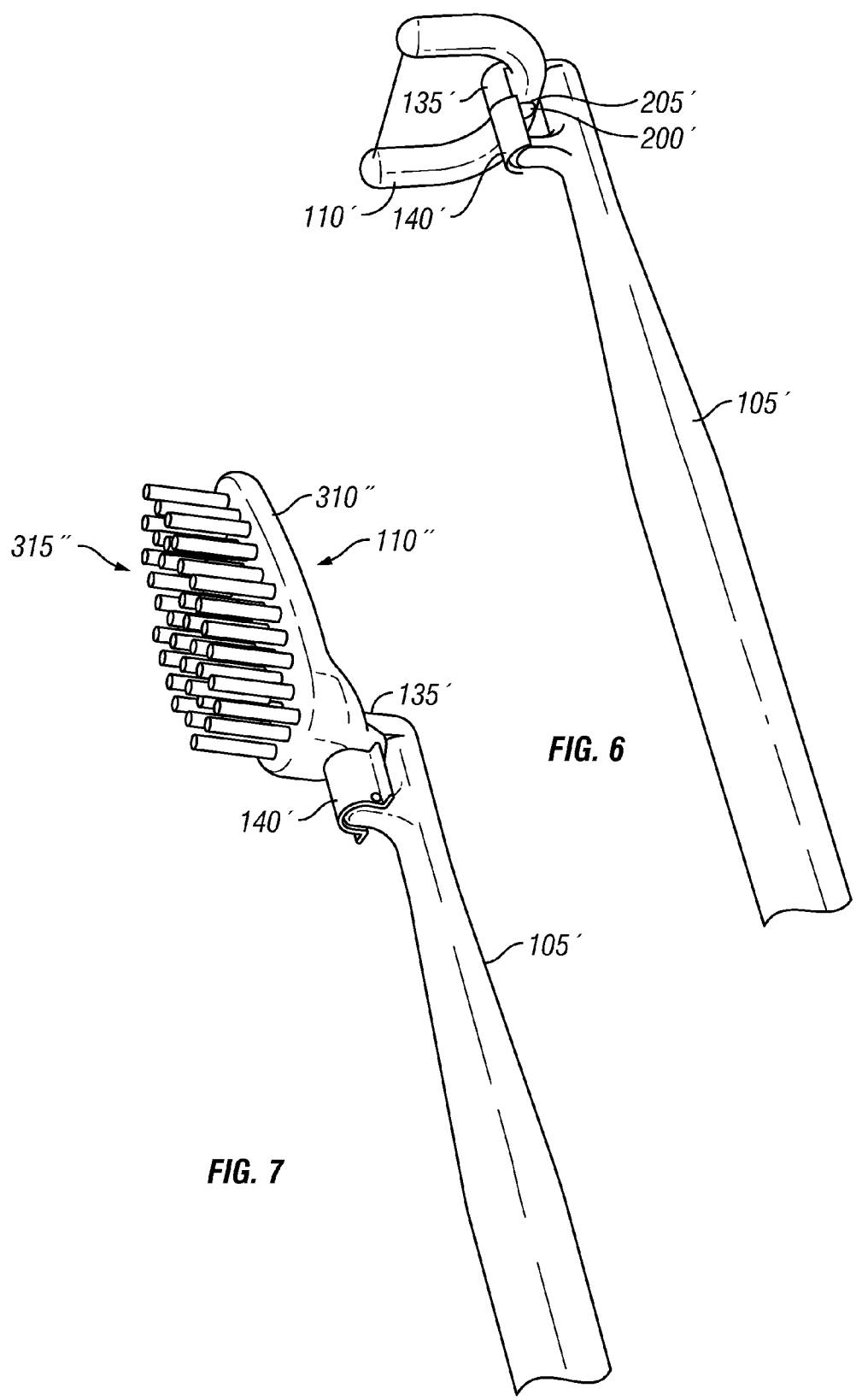

ORAL HYGIENE SYSTEM

CROSS-REFERENCE TO RELATED APPLICATIONS

This application claims benefit of U.S. provisional application Ser. No. 61/313,248 filed Mar. 12, 2010, and entitled "Flossing System," which is hereby incorporated herein by reference in its entirety for all purposes.

STATEMENT REGARDING FEDERALLY SPONSORED RESEARCH OR DEVELOPMENT

Not applicable.

BACKGROUND

The disclosure relates generally to a system for oral hygiene, including flossing and brushing teeth. More particularly, the disclosure relates to a two-piece oral hygiene system including a handle for receiving a replaceable oral hygiene attachment.

Flossing and brushing are essential to good oral hygiene. While brushing is an effective way to clean teeth, it reaches only approximately sixty percent of the teeth. Flossing is also needed to reach areas of the teeth that brushing cannot, in particular the areas between teeth. Approximately seventy percent of cavities occurring in children seven years old or younger are located in the areas between adjacent teeth. Even so, flossing is not generally practiced as often as brushing, in part because it can be more time consuming than brushing and because it is a comparatively more difficult task, especially for children.

Embodiments of the present invention are directed to a two-piece oral hygiene system that seeks to overcome these and other limitations of the prior art.

BRIEF DESCRIPTION OF THE DRAWINGS

For a detailed description of the disclosed embodiments, reference will now be made to the accompanying drawings in which:

FIG. 6 is a perspective view of the alternative handle of FIG. 5 with an alternative floss attachment; and FIG. 7 is a perspective view of an alternative brush attachment.

DETAILED DESCRIPTION OF THE DISCLOSED EMBODIMENTS

Figure 1:
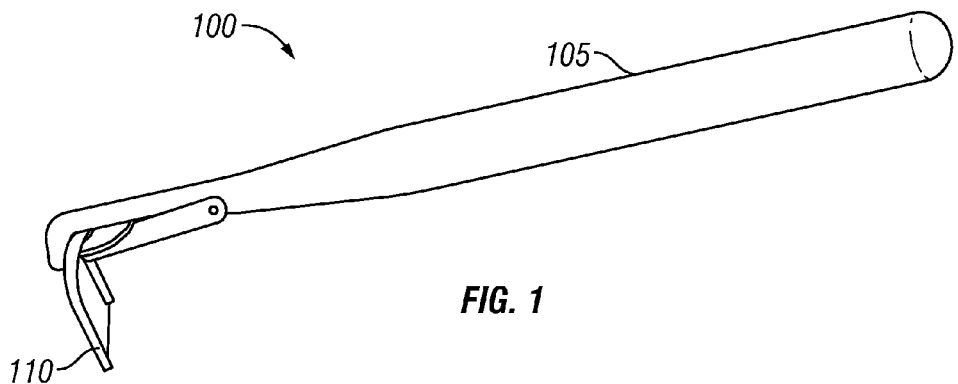
FIG. 1 is a perspective view of an oral hygiene system in accordance with the principles disclosed herein.

The following description is directed to exemplary embodiments of an oral hygiene system and associated methods. The embodiments disclosed should not be interpreted, or otherwise used, as limiting the scope of the disclosure, including the claims. One skilled in the art will understand that the following description has broad application, and that the discussion is meant only to be exemplary of the described embodiments, and not intended to suggest that the scope of the disclosure, including the claims, is limited to those embodiments.

Certain terms are used throughout the following description and the claims to refer to particular features or components. As one skilled in the art will appreciate, different persons may refer to the same feature or component by different names. This document does not intend to distinguish between components or features that differ in name but not function. Moreover, the drawing figures are not necessarily to scale. Certain features and components described herein may be shown exaggerated in scale or in somewhat schematic form, and some details of conventional elements may not be shown in interest of clarity and conciseness.

In the following discussion and in the claims, the terms "including", "comprising", and "having" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices and connections. Further, the terms "axial" and "axially" generally mean along or parallel to a central or longitudinal axis, while the terms "radial" and "radially" generally mean perpendicular to the central or longitudinal axis.

Referring now to FIG. 1, there is shown an oral hygiene system in accordance with the principles disclosed herein. Oral hygiene system 100 includes a handle 105 and a floss attachment 110. As will be described, handle 105 receives an oral hygiene attachment 110, for example the floss attachment shown such that oral hygiene attachment 110 cannot move relative to handle 105. Thus, in the example shown, the floss attachment cannot detach from handle 105 during use. In particular, oral hygiene attachment 110 cannot slip relative to handle 105 within the mouth of someone using system 100 or detach from handle 105 within the individual's mouth.

Figure 2A:
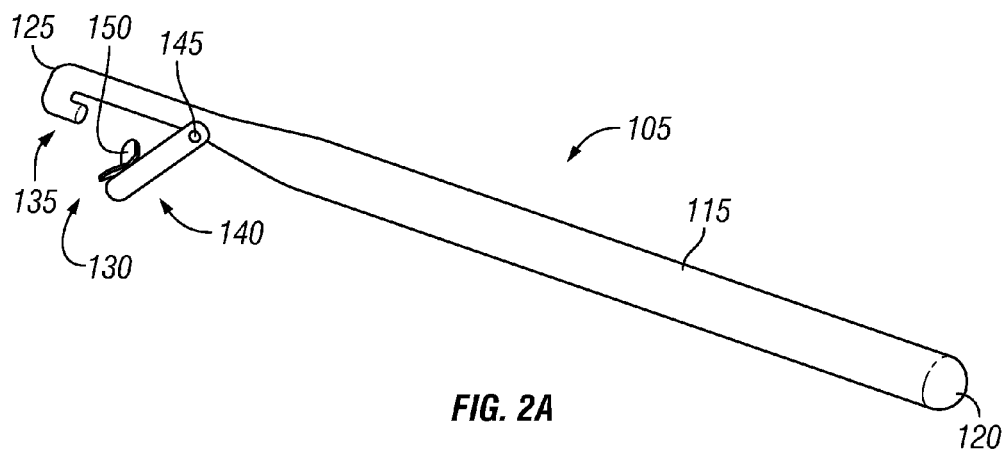
FIGS. 2A and 2B are perspective views of the handle of FIG. 1.
Figure 2B:
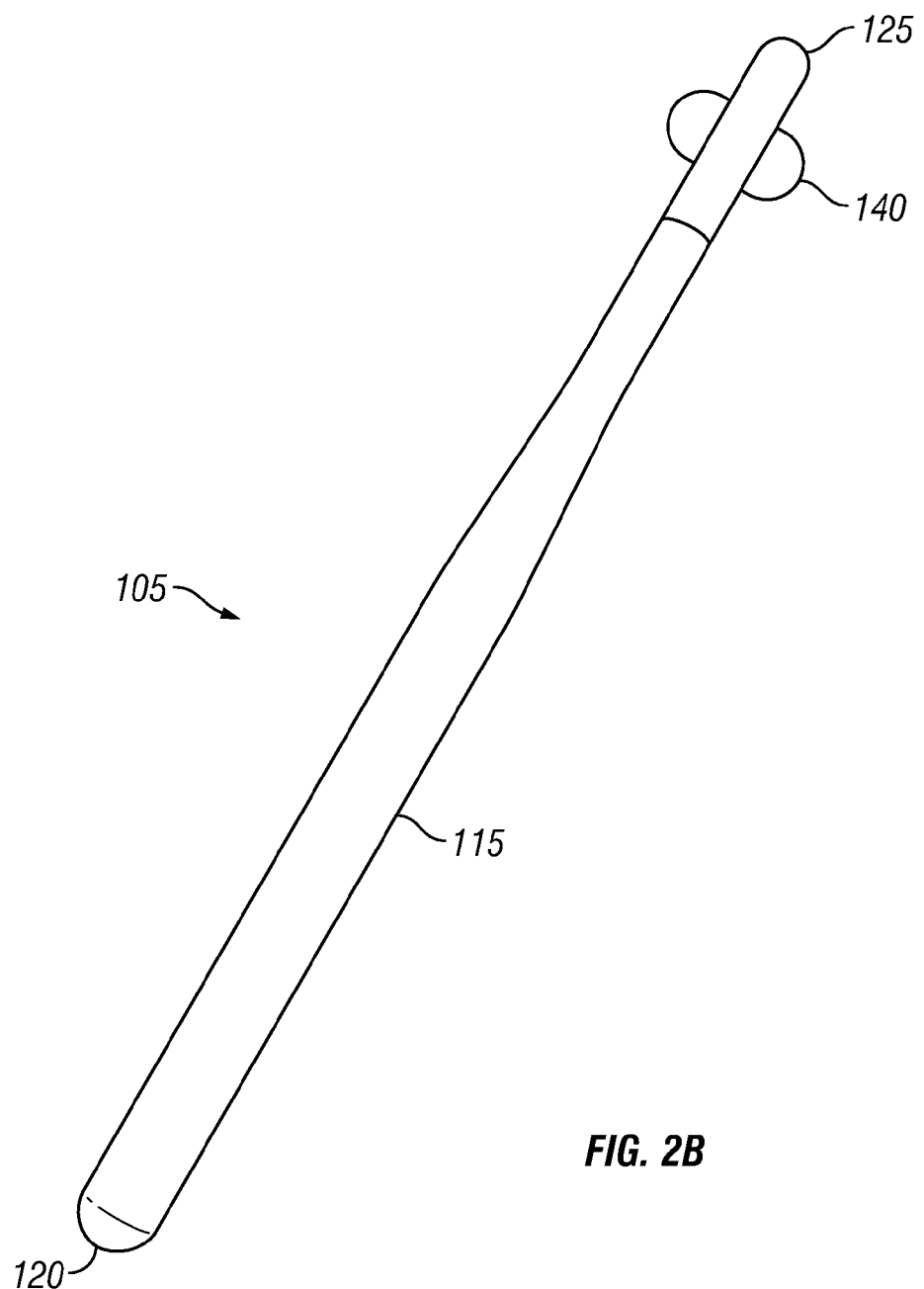

Turning to FIGS. 2A and 2B, handle 105 has a substantially cylindrical body 115 extending between two ends 120, 125. Further, the diameter of body 115 at end 120 is greater than the diameter of body 115 at end 125, and body 115 is tapered therebetween. The tapering of body 115 enables gripping of body 115 proximate end 120, and insertion of end 125 into the mouth of a user. In some embodiments, handle 105 comprises plastic.

At end 125, handle 105 further includes a releasable locking mechanism 130. Locking mechanism 130 includes a locking receptacle 135 and a safety gate 140. Safety gate 140 is moveable relative to handle 105 to couple, or lock, with receptacle 135 and to decouple, or unlock, from receptacle 135. When safety gate 140 is unlocked from receptacle 135 and moved away from receptacle 135, oral hygiene attachment 110 (FIG. 1) may be coupled to or removed from handle 105, as will be described. Alternatively, when safety gate 140 is locked to receptacle 135 with oral hygiene attachment 110 coupled to handle 105, oral hygiene attachment 110 may not move relative to, or detach from, handle 105.

In the illustrated embodiment, locking receptacle 135 is a small recess formed in end 125 of handle 105. Safety gate 140 is coupled to handle 105 via a hinge or pin 145 extending through handle 105 and is pivotable relative to handle 105 about the longitudinal axis of pin 145. Further, safety gate 140 has a nodule 150 which, upon application of some compression load to safety gate 140, snaps into locking receptacle 135 and, upon application of some tension thereafter to safety gate 140, unsnaps from locking receptacle 135. When safety gate 140 is pivoted relative to locking receptacle 135 and nodule 150 of safety gate 140 is snapped into locking receptacle 135, safety gate 140 is coupled, or locked, with locking receptacle 135, as shown in FIG. 1. When nodule 150 is unsnapped from receptacle 135, safety gate 140 is decoupled, or unlocked, from locking receptacle 135. Also, when safety gate 140 is pivoted away from locking receptacle 135, as shown in FIG. 2A, oral hygiene attachment 110 may be coupled to or decoupled from handle 105.

Figure 3:
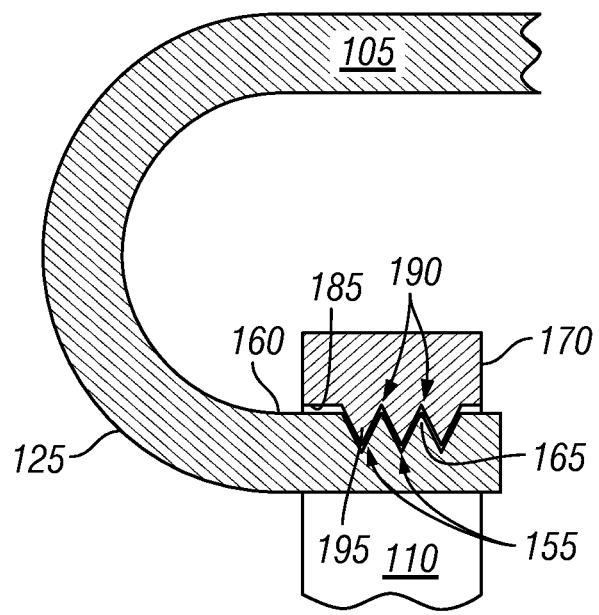
FIG. 3 is a schematic cross-sectional view of the floss attachment of FIG. 1 interlocked with the handle of FIG. 1.

End 125 of handle 105 is preferably curved or hook-shaped, as best viewed in FIG. 2A. Referring briefly to FIG. 3, handle 105 includes a surface profile that includes one or more grooves 155 formed in the interior surface 160 of end 125. Between each pair of adjacent grooves 155, a tooth 165 is formed. As will be described, grooves 155 and teeth 165 enable coupling of floss attachment 110 with handle 105.

Figure 4:
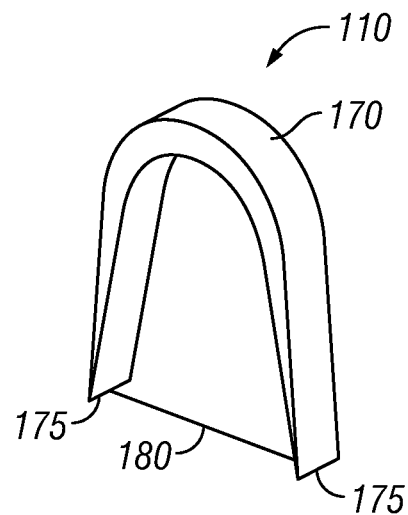
FIG. 4 is a perspective view of a floss attachment of FIG. 1.

Referring now to FIG. 4, oral hygiene attachment 110 in the form of a floss attachment includes a substantially U-shaped body 170 extending between two ends 175 and a string or thread of flossing material 180 extending between ends 175. In some embodiments, body 170 comprises plastic. As best viewed in FIG. 3, body 170 includes an interior surface 185 having a surface profile that includes one or more grooves 190 formed therein. Between each pair of adjacent grooves 190, a tooth 195 is formed. Grooves 190 and teeth 195 enable coupling of oral hygiene attachment 110 to handle 105. Specifically, surface profile of oral hygiene attachment 110 and the surface profile of handle 105 are configured such that each groove 190 receives a tooth 165 of handle 105 and each groove 155 receives a tooth 195 of oral hygiene attachment 110 when oral hygiene attachment 110 is seated against handle 105, as illustrated. In other words, the surface profiles interlock, and when interlocked, oral hygiene attachment 110 does not move relative to handle 105.

Figure 5:
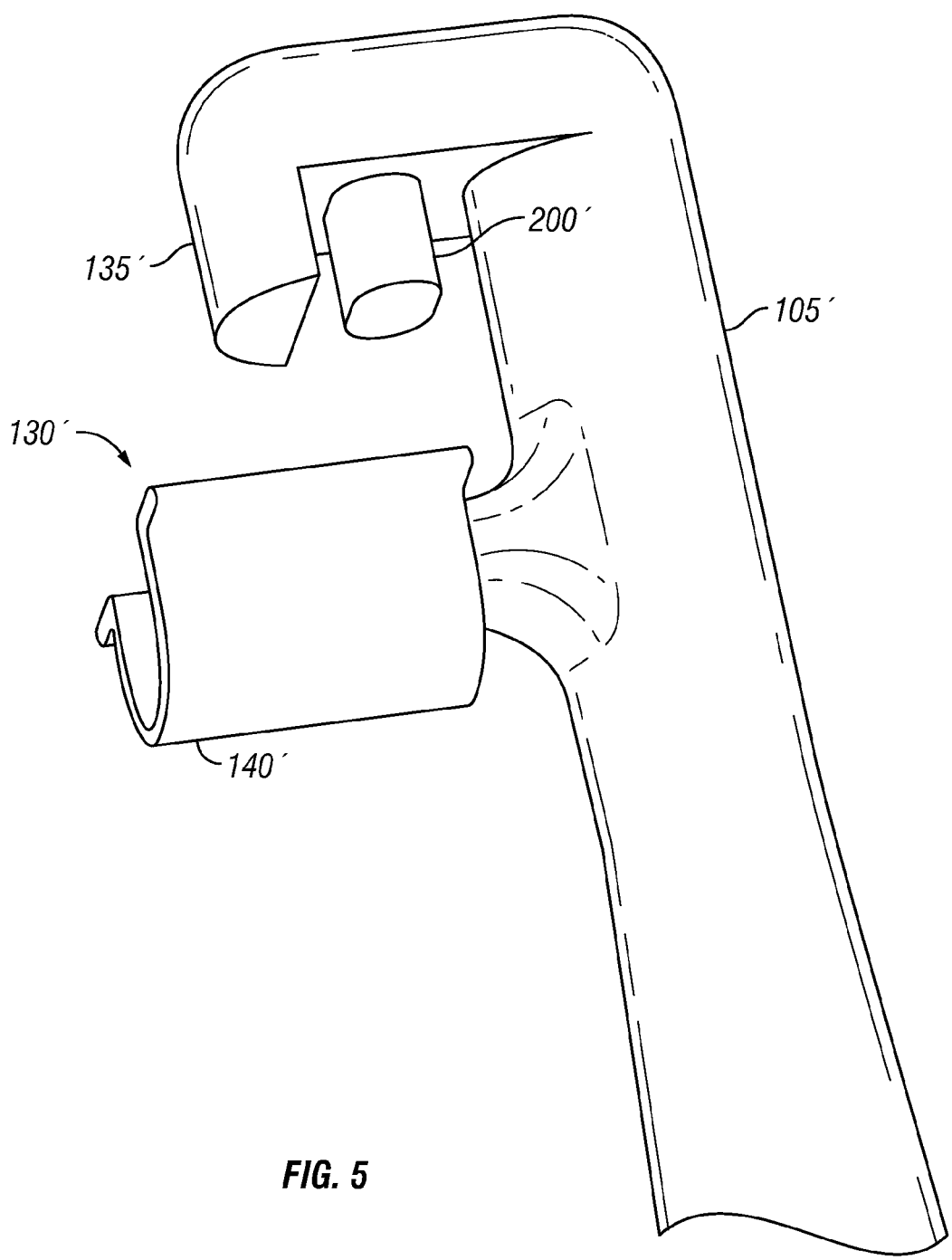
FIG. 5 is a perspective view of an alternative handle.

Referring now to FIGS. 5 and 6, an alternative embodiment handle 105' further includes an alternative embodiment releasable locking mechanism 130'. Locking mechanism 130' also includes a locking receptacle 135' and a safety gate 140'. Safety gate 140' is moveable relative to handle 105' to couple, or lock, with receptacle 135' and to decouple, or unlock, from receptacle 135'. When safety gate 140' is unlocked from receptacle 135' and moved away from receptacle 135', an alternative embodiment oral hygiene attachment 110' (FIG. 6) may be coupled to or removed from handle 105', as will be described. Alternatively, when safety gate 140' is locked to receptacle 135' with oral hygiene attachment 110' coupled to handle 105', oral hygiene attachment 110' may not move relative to, or detach from, handle 105'.

In the illustrated embodiment, locking receptacle 135' is formed on the handle 105' with a curved outer surface facing the safety gate 140'. Safety gate 140' is coupled to handle 105' so that safety gate 140' can pivot relative to handle 105'. Further, safety gate 140' has a curved surface which, upon application of some compression load to safety gate 140', snaps or otherwise interference fits onto the curved surface of the locking receptacle 135' and, upon application of some tension thereafter to safety gate 140', unsnaps from locking receptacle 135'. When safety gate 140' is pivoted relative to locking receptacle 135' and is snapped onto locking receptacle 135', safety gate 140' is coupled, or locked, with locking receptacle 135'. When safety gate 140' is unsnapped from receptacle 135', safety gate 140' is decoupled, or unlocked, from locking receptacle 135'. Also, when safety gate 140' is pivoted away from locking receptacle 135', as shown in FIG. 5, oral hygiene attachment 110' may be coupled to or decoupled from handle 105'.

As with the previous embodiment handle 105' and oral hygiene attachment 110' include surface profiles that enable coupling of oral hygiene attachment 110' with handle 105'. As shown, the surface profile of the handle 105' includes a post 200' extending from handle 105'. Oral hygiene attachment 110' includes a corresponding recess 205' that may or may not extend through oral hygiene attachment 110'.

Post 200' and recess 205' enable coupling of oral hygiene attachment 110' to handle 105'. Specifically, recess 205' receives the post 200' when oral hygiene attachment 110' is seated against handle 105' such that post 200' and recess 205' interlock. When interlocked, oral hygiene attachment 110' does not move relative to handle 105'. Additionally, oral hygiene attachment 110' may not include a recess but instead include a flat surface facing post 200' and be dimensioned to fit against post 200' so that when coupled to handle 105' such that floss attachment 110' may not move relative to handle 105'.

To use oral hygiene system 100, locking mechanism 130 or 130' of oral hygiene system 100 is unlocked and safety gate 140 or 140' is manually pivoted away from locking receptacle 135 or 135', as shown in FIGS. 2A and 5. Oral hygiene attachment 110 is then coupled to end 125 of handle 105 with teeth 165 of handle 105 received within grooves 190 of oral hygiene attachment 110 and teeth 195 of oral hygiene attachment 110 received within grooves 155 of handle 105. Alternatively, oral hygiene attachment 110' is then coupled to the end 125 of handle 105' with the recess 205' receiving the post 200'. When oral hygiene attachment 110, 110' is interlocked with handle 105, 105', safety gate 140, 140' is manually pivoted and locked with receptacle 135, 135', as previously described. Oral hygiene system 100 is then ready for use.

During use of the oral hygiene attachment in the form of the floss attachment, flossing material 180 may be inserted between adjacent teeth to promote cleaning. Even so, the motion of flossing with any of these components 180 will not cause oral hygiene attachment 110, 110' to move relative to handle 105, 105' due to the engagement of the surface profiles. Also, the motion of flossing will not cause safety gate 140, 140' to inadvertently disengage end 125 of handle 105, 105'. After use, oral hygiene attachment 110, 110' may be removed from handle 105, 105' and disposed of.

Referring now to FIG. 7, an alternative embodiment oral hygiene attachment 110" is shown. Instead of a floss attachment, oral hygiene attachment 110" is a tooth brush attachment attached to the end 135' of the handle 105' that includes a body 310" and bristles 315"'. Oral hygiene attachment 110" is shown coupled to handle 105' using locking mechanism 140' and surface profiles similar to locking mechanism 140' and surface profiles shown in FIGS. 5 and 6. Although the locking mechanism and surface profiles shown are similar to the embodiment of handle 105' shown in FIGS. 5 and 6, any of the locking mechanisms and surface profiles discussed above may be used.

While various embodiments have been shown and described, modifications thereof can be made by one skilled in the art without departing from the spirit and teachings herein. The embodiments herein are exemplary only, and are not limiting. Many variations and modifications of the apparatus disclosed herein are possible and within the scope of the invention. Accordingly, the scope of protection is not limited by the description set out above, but is only limited by the claims which follow, that scope including all equivalents of the subject matter of the claims.

What is claimed is:

1. An oral hygiene system comprising:
a handle comprising a central axis, a first end, and a second end opposite the first end;

a locking receptacle disposed at the first end of the handle, the locking receptacle comprising a first section extending radially from the first end of the handle and a second section extending axially from the first section, wherein the second section is radially spaced from the handle;

a post radially spaced from the handle and extending axially from the first section of the locking receptacle, wherein the post is radially positioned between the second section of the locking receptacle and the handle;

an oral hygiene attachment configured to engage both the post and the second section; and a safety gate pivotally coupled to the handle, wherein the safety gate has a first position engaging the second section of the locking receptacle and a second position pivoted away from the second section of the locking receptacle.

2. The oral hygiene system of claim 1, wherein the safety gate further comprises a nodule and the locking receptacle is configured to receive the nodule.

3. The oral hygiene system of claim 1, wherein the safety gate comprises a curved surface that snaps onto the second section of the locking receptacle.

4. The oral hygiene system of claim 1, wherein the locking receptacle prevents movement of the oral hygiene attachment relative to the handle when the safety gate is in the first position.

5. The oral hygiene system of claim 4, wherein the oral hygiene attachment comprises a surface profile that prevents movement of the oral hygiene attachment relative to the handle.

6. The oral hygiene system of claim 5, wherein the surface profiles comprise interlocking grooves and teeth.

7. The oral hygiene system of claim 5, wherein the oral hygiene attachment surface profile comprises a recess configured to slidingly engage with the post.

8. The oral hygiene system of claim 1, wherein the oral hygiene attachment comprises a floss attachment comprising a substantially U-shaped body between two ends with flossing material extending between the ends.

9. The oral hygiene system of claim 1, wherein the oral hygiene attachment comprises a tooth brush attachment.

10. A kit of parts forming an oral hygiene system, the kit of parts comprising:

a handle comprising a central axis, a first end, and a second end opposite the first end;

a locking receptacle disposed at the first end of the handle;

a safety gate pivotally coupled to the handle between the first and second end and proximate the first end; and an oral hygiene attachment removably coupled to the locking receptacle;

wherein the safety gate has a first position engaging the locking receptacle and a second position disengaged from the locking receptacle;

wherein the locking receptacle prevents movement of the oral hygiene attachment relative to the handle when the safety gate is in the first position;

wherein the oral hygiene attachment comprises a surface profile that prevents movement of the oral hygiene attachment relative to the handle.

11. The kit of parts of claim 10, wherein the safety gate further comprises a nodule and the locking receptacle is configured to receive the nodule.

12. The kit of parts of claim 10, wherein the safety gate comprises a curved surface that snaps onto the locking receptacle.

13. The kit of parts of claim 10, wherein the surface profiles comprise interlocking grooves and teeth.

14. The kit of parts of claim 10, further comprising a post extending axially from the locking receptacle, and wherein the oral hygiene attachment comprises a recess configured to slidingly engage the post.

15. The kit of parts of claim 10, wherein the oral hygiene attachment comprises a floss attachment comprising a substantially U-shaped body between two ends with flossing material extending between the ends.

16. The oral hygiene system of claim 10, wherein the oral hygiene attachment comprises a tooth brush attachment.

17. A method for assembling an oral hygiene system, the method comprising:

opening a safety gate pivotally coupled to a handle, the handle having a central axis, a first end, a second end opposite the first end;

removably coupling an oral hygiene attachment to a locking receptacle disposed at the first end of the handle, the locking receptacle including a first section extending radially from the first end of the handle and a second section extending axially from the first section, wherein the second section is radially spaced from the handle; and closing the safety gate to engage the second section of the locking receptacle;

wherein coupling the oral hygiene attachment onto the locking receptacle comprises interlocking surface profiles of the oral hygiene attachment and the locking receptacle.

\* \* \* \* \*